United States Patent
Cunningham et al.

(10) Patent No.: US 7,809,424 B2
(45) Date of Patent: Oct. 5, 2010

(54) METHOD OF OFF-RESONANCE DETECTION USING COMPLEMENTARY MR CONTRAST AGENTS

(75) Inventors: Charles H. Cunningham, San Francisco, CA (US); Steven M. Conolly, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1364 days.

(21) Appl. No.: 11/271,593

(22) Filed: Nov. 10, 2005

(65) Prior Publication Data

US 2007/0104650 A1    May 10, 2007

(51) Int. Cl.
*A61B 5/05* (2006.01)
(52) U.S. Cl. .................................. 600/411; 424/9.3
(58) Field of Classification Search .................. 600/410, 600/411, 420, 424, 431; 324/201, 204, 214, 324/215, 307, 309; 424/9.3, 9.323, 9.1
See application file for complete search history.

(56) References Cited

U.S. PATENT DOCUMENTS 7,502,640 B2 * 3/2009 Conolly et al. .............. 600/411

2005/0261575 A1    11/2005   Conolly

OTHER PUBLICATIONS

Cunningham et al. Positive Contrast Magnetic Resonance Imaging of Cells Labeled with Magnetic Nanoparticles. Magnetic Resonance in Medicine. 53:999-1005. 2005.*
Weissleder R et al. Magnetically labeled cells can be detected by MR imaging. Journal of Magnetic Resonance Imaging. 7:258-263. 1997.*
Schenck JF et al. The role of magnetic susceptibility in magnetic resonance imaging: MRI magnetic compatibility of the first and second kinds. Med Phys. 23:815-843. 1996.*
Frank JA et al. Clinically applicable labeling of mammalian and stem cells by combining superparamagnetic iron oxides and transfection agents. Radiology. 228:480-487. 2003.*

* cited by examiner

*Primary Examiner*—Brian Casler
*Assistant Examiner*—Parikha S Mehta
(74) *Attorney, Agent, or Firm*—Beyer Law Group LLP

(57) ABSTRACT

Off-resonance imaging uses two complementary contrast agents with the first agent (iron-oxide) particles transfected into cells which provide localized signals. The second agent is detected from a change in the off-resonance signal when present in the cells labeled by the first agent.

18 Claims, 3 Drawing Sheets

METHOD OF OFF-RESONANCE DETECTION USING COMPLEMENTARY MR CONTRAST AGENTS

GOVERNMENT RIGHTS

This invention was made with Government support under contract R01HL067161-01A2 awarded by the National Institutes of Health. The Government has certain rights in this invention.

CROSS REFERENCE TO RELATED APPLICATIONS

This patent application is related to our commonly assigned application Ser. No. 10/849,068, filed May 18, 2004, now U.S. Pat. No. 7,502,640 issued on Mar. 10, 2009, for "Positive Contrast MRI of Magnetically Tagged Cells, Objects, Tissues." which is incorporated herein by reference for all purposes.

BACKGROUND OF THE INVENTION

This invention relates generally to nuclear magnetic resonance (NMR) and to magnetic resonance imaging (MRI), and more particularly the invention relates to the use of MR in tracking magnetically labeled cells or objects using positive contrast.

Contrast agents incorporating super-paramagnetic iron-oxide (SPIO) nanoparticles have shown much promise as a means to visualize labeled cells using MRI. The small size of the particles (<100 nm) facilitates transport across cell membranes, and the low toxicity allows for large iron loads without significant cell death (e.g., 25 pg/cell). Labeling can be performed by incubating cells of interest (e.g., embryonic stem cells) with the contrast agent in vitro, so that they can be monitored in vivo using MRI. Cells such as macrophages can be labeled in vivo by introducing the contrast agent into the bloodstream, with the uptake of the agent occurring by phagocytosis, which has been used to image atherosclerosis and other inflammatory processes. In more advanced schemes, SPIO-protein complexes that bind to the receptors on specific cells have been used.

Cells loaded with SPIO cause significant signal dephasing due to the magnetic field inhomogeneity induced in water molecules near the cell. These manifest as signal voids in the image. With the signal void as the means for detection, the particles are behaving as a negative contrast agent, as opposed to positive contrast agents such as gadolinium chelates that brighten the local signal intensity by shortening T1. A fundamental drawback of negative contrast agents is that the agent cannot be distinguished from a void in the image. Moreover, negative contrast agents suffer from partial-volume effects, where the ability to detect a void depends critically on the resolution of the image; voxel size must be smaller than the void volume for reliable visualization. While it is possible to achieve positive contrast with SPIOs by employing T1 weighting, this is only possible with the smaller-sized particles (10-50 nm) and can be inefficient because of competing T1 and T2* effects.

Co-pending application Ser. No. 10/849,068, supra, discloses a new method for imaging objects and materials that cause a localized magnetic field inhomogeneity in an MRI scanner with positive contrast. In one embodiment of the method, spectrally-selective RF pulses are used to excite and refocus the off-resonance water surrounding the cells labeled with SPIO agents, while suppressing on-resonance signal, so that only the fluid and tissue immediately adjacent to the labeled cells are visible in the image.

The present invention provides an enhancement to the off-resonance method which alleviates problems associated with background signal noise.

SUMMARY OF THE INVENTION

The invention provides a magnetic resonance method for identifying the presence and location in a body of a targeted contrast agent by first labeling cells with magnetic susceptibility nano particles such as iron oxide, then applying a sequence of RF excitation for a narrow band of frequencies near the labeled cells, which provides a baseline off-resonance signal for the labeled cells.

A second contrast agent is then administered, and presence of the second contrast agent near the labeled cells is identified by detecting any effect of the second contrast agent in the off-resonance signal.

Thus, at least two complementary contrast agents are employed with the first contrast agent providing a localized signal and the second contrast agent, after being administered, being detectable in the localized signal.

The invention and object and features thereof will be more readily apparent from the following detailed description and appended claims when taken with the drawings.

DETAILED DESCRIPTION OF THE PREFERRED EMBODIMENTS

As described in U.S. Pat. No. 7,502,640, supra, a collection of labeled cells will cast a field pattern in the water molecules immediately surrounding the cells. The field pattern can be approximated by a dipole field from a magnetized sphere. The dipole pattern demonstrates a classic field cross pattern, in which the local $B_z$ field is enhanced in the north and south poles and suppressed along the equator. The polarity of the field perturbation would be reversed for a diamagnetic agent. The dipole field pattern intensity falls off quickly. The field perturbation varies as $$\Delta B_z(r, \theta) = \frac{\Delta \chi B_O}{3}\left(\frac{a}{r}\right)^3 (3\cos^2\theta - 1) \qquad (1)$$

where $\Delta\chi$ is the difference in bulk magnetic susceptibility between the sphere and surroundings, $a$ is the radius of the sphere, $r$ is the distance from the sphere center, and $\theta$ is the angle relative to the main field, $B_o$. Hence, the field pattern from a smaller collection of cells will fall off more steeply than that from a larger collection. In practice, agglomerations of labeled cells may not be spherical, but this theory can be applied to the general case by summing the patterns from a group of spheres. For most superparamagnetic particles, the magnetization saturates at about 0.2 T, so that the linear dependence on BO can be expressed as a fixed remnant magnetization.

Figure 1A:
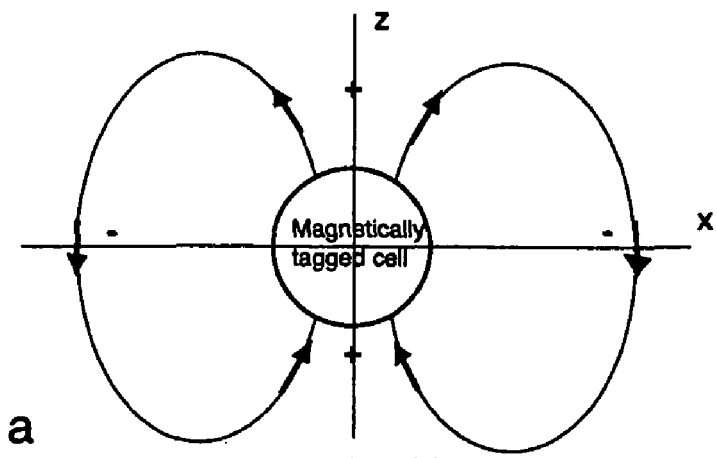
FIGS. 1a-1c illustrate magnetic field lines induced outside a magnetized sphere; regions of excitation for a RF pulse with carrier frequency $W_S$ and bandwidth BW; and isofrequency contours surrounding a magnetized sphere.
Figure 1B:
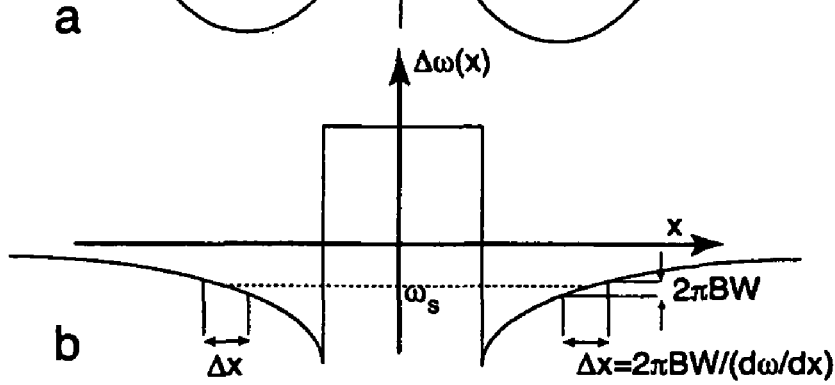
Figure 1C:
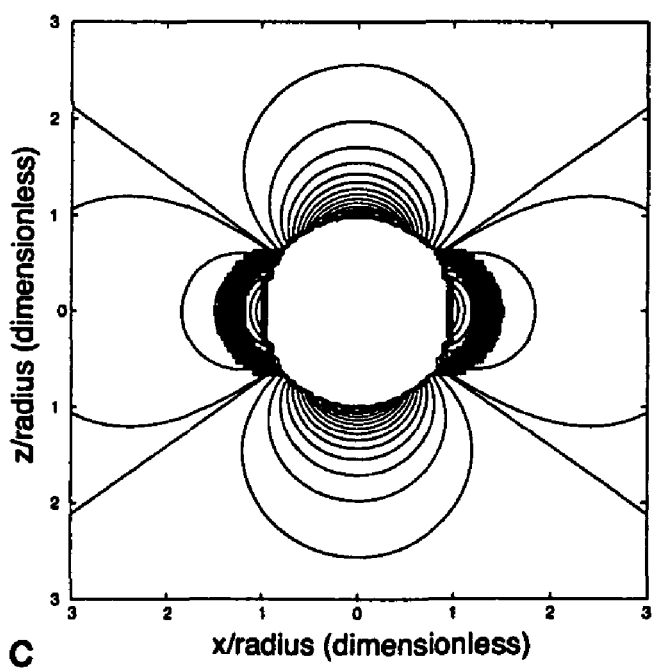

Instead of using the field gradient cast by the labeled cells to de-phase the NMR signal from nearby water molecules, we use this gradient to selectively excite and refocus a narrow band of water molecules. This is similar in concept to slice-selective excitation, where a narrowband RF pulse is applied in the presence of a linear field gradient to select a particular slice. There are some notable differences: the field cast by a labeled cell is extremely localized and nonlinear. However, the pulse sequence is designed to extend the slice-selection concept to excite/refocus a thin shell of spins located at a particular frequency offset from the magnetized cells. FIG. 1 illustrates the concept. In FIG. 1(a), the magnetic-field lines induced outside a magnetized sphere. In FIG. 1(b), by applying an RF pulse with carrier frequency $\omega_S$ and bandwidth BW, the regions with thickness $\Delta\chi$ are excited. In FIG. 1(c), isofrequency contours surrounding a magnetized sphere ($\Delta\chi=-500$ ppm) are shown, with the shaded regions showing the spatial extent of the regions that would be excited by a band-selective RF pulse with $\omega_{s=-}150$ ppm and BW=100 ppm. Similar to conventional slice selection, a spatial shell of water is excited using the intense microgradient. Since only this shell is excited, the image demonstrates positive contrast. Note that positive frequency shifts will excite spins at the poles (where the field is enhanced) and negative frequency shifts will excite spins at the equator (where the field is diminished). A symmetric (cos-modulated) RF pulse will excite both the poles and the equator. The spatial distribution of this signal will be that of an "onion layer". Note that in conventional slice selection the gradient is refocused by a negative lobe of half the duration. Because it is impossible to negate the gradient due to a magnetic particle, spin-echo refocusing pulses are currently thought to be critical.

There are several pulse-sequence parameters that can affect the quality of the positive contrast images. The key parameters are: the excitation profiles' shape (bandwidth, transition width, ripples), the center-frequency shift, and the echo time. These parameters are linked and the tradeoffs are discussed below.

The excitation profiles of the frequency selective RF pulses must be carefully designed to achieve good contrast-to-noise. For a fixed bandwidth of excitation pulses, the largest volume of water will be excited for each cell by minimizing the off-resonance shift, as shown in FIG. 1. This excites the largest-radius shell of tissue or fluid. However, there is a tradeoff in contrast: if the frequency is set too close to on-resonance resonance water, then excitation of background spins could occur because water could be shifted into the passband by field inhomogeneities. For adequate background suppression, the "out-of-slice" ripple of the RF pulses is also a concern. These ripples can be made small at the expense of wider transition widths.

For fixed off-resonance frequency, the bandwidth of the RF pulses determines the thickness of the shell excited. For a maximal volume of magnetization, the excitation bandwidth would be set as wide as possible. It is because of this wide bandwidth that the T2* decay is rapid and a spin-echo sequence is crucial. However, there is a tradeoff because wide bandwidth implies that the T2* decay of the spin echo will be extremely short, which will limit sensitivity and resolution. Hence a different, optimal RF bandwidth for different sized groups of cells is expected.

Another important challenge is diffusion: the field gradient immediately outside a single, small SPIO particle is enormous. Diffusion of the excited water molecules near the labeled cells could cause significant, irreversible signal dephasing. However, it is known that with conventional pulse sequences, the signal loss in vicinity of sufficiently loaded cells is governed by the "static dephasing regime" theory, in which diffusional losses are minor. Since the new method images spins which are not visible with conventional methods, the appropriate theoretical model for the relaxation properties of these spins remains unclear. In theory, the effects of diffusion can be reduced by minimizing both the center-frequency shift and the echo time. A potential tradeoff exists because longer RF pulses can excite sharper profiles, and can therefore be moved closer to resonance (where the gradients are less steep), but the increase in echo time could increase diffusion losses.

Figure 2:
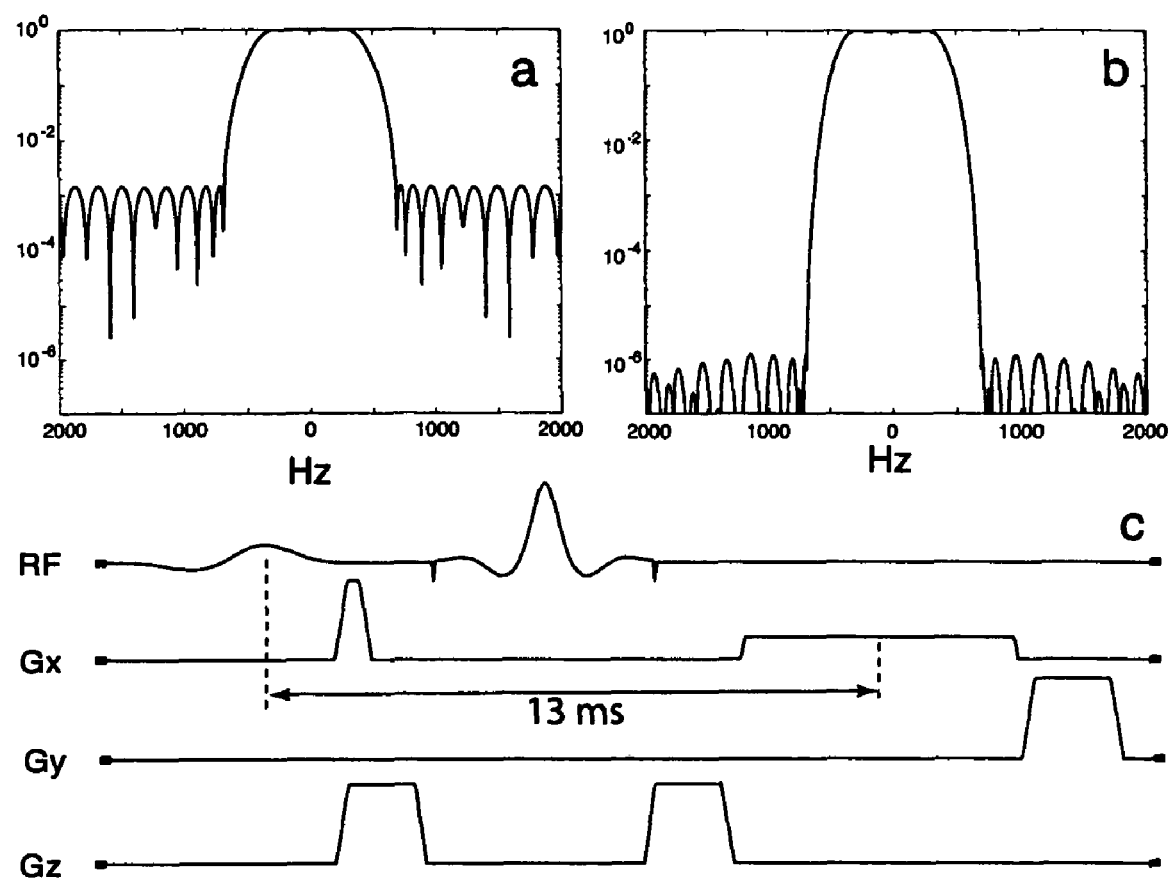
FIG. 2 illustrates a pulse sequence for positive-contrast imaging of tagged cells in accordance with an embodiment of the invention and a pulse sequence for a minimum echo line with short readout to minimize blurring associated with a wideband echo.

Spectrally-selective RF pulses were designed using the Shinnar-Le Roux (SLR) algorithm implemented in MAT-LAB (The Mathworks Inc., Natick, Mass.). By matching the profiles of a 90-degree excitation and a 180-degree refocusing pulse, a spin-echo sequence with million-fold (120 dB) suppression of on-resonance water was designed as shown in FIG. 2 FIG. 2 shows a pulse sequence for positive-contrast imaging of magnetically tagged cells. (a) The profile for each of the 5 ms RF pulses was designed to excite/refocus a 1 kHz passband with 0.1% out-of-slice ripple. (b) The profile for the combined 90-180 pair gives million-fold suppression of on-resonance water. (c) The pulse sequence allows a minimum echo time of 13 ms, with a short (4 ms) readout to minimize the blurring associated with the wideband echo. This pulse sequence was implemented on a GE Signa 1.5T whole-body MRI system (General Electric Medical Systems, Waukesha, Wis.).

Cell labeling solution was prepared by mixing cell culture medium with 25 µg/mL of the SPIO Feridex (Advanced Magnetics, Cambridge, Mass.) and 375 ng/mL of poly-l-lysine (Sigma, St. Louis, Mo.) at room temperature for 60 minutes. The embryonic stem cell (ESC) line TL-1 was derived from 129 Sv/J mice and cultured in a medium consisting of high-glucose Dulbecco's modified Eagles Medium with L-glutamate glutamate (Specialty Media, Pillipsburg, N.J.), 10% ESC qualified fetal bovine serum (Invitrogen, Carlsbad, Calif.), and 1% penicillin/streptomycin solution (Invitrogen, Carlsbad, Calif.). Prior to injection, the cells were incubated with the labeling solution for 12-24 hours. The cell cultures were then transferred to centrifuge tubes and subjected to three cycles of centrifuge, each time followed by dilution with phosphate-buffered saline solution to wash away any extracellular SPIO.

In accordance with the present invention, the off-resonance signal described above is used to detect the presence of at least a second contrast agent that will give additional information. The second agent can be selected from a group of agents such as, for example, gadolinium, hyperpolarized carbon-13, and T1 shortening agents such as Combidex.

Prior to administering the second contrast agent, a baseboard signal is obtained using the off-resonance method with a first contrast agent labeling cells. The second contrast agent is then administered, and a presence of the second contrast agent in the labeled cells is detected by observing effects in the off-resonance baseline signal.

Figure 3:
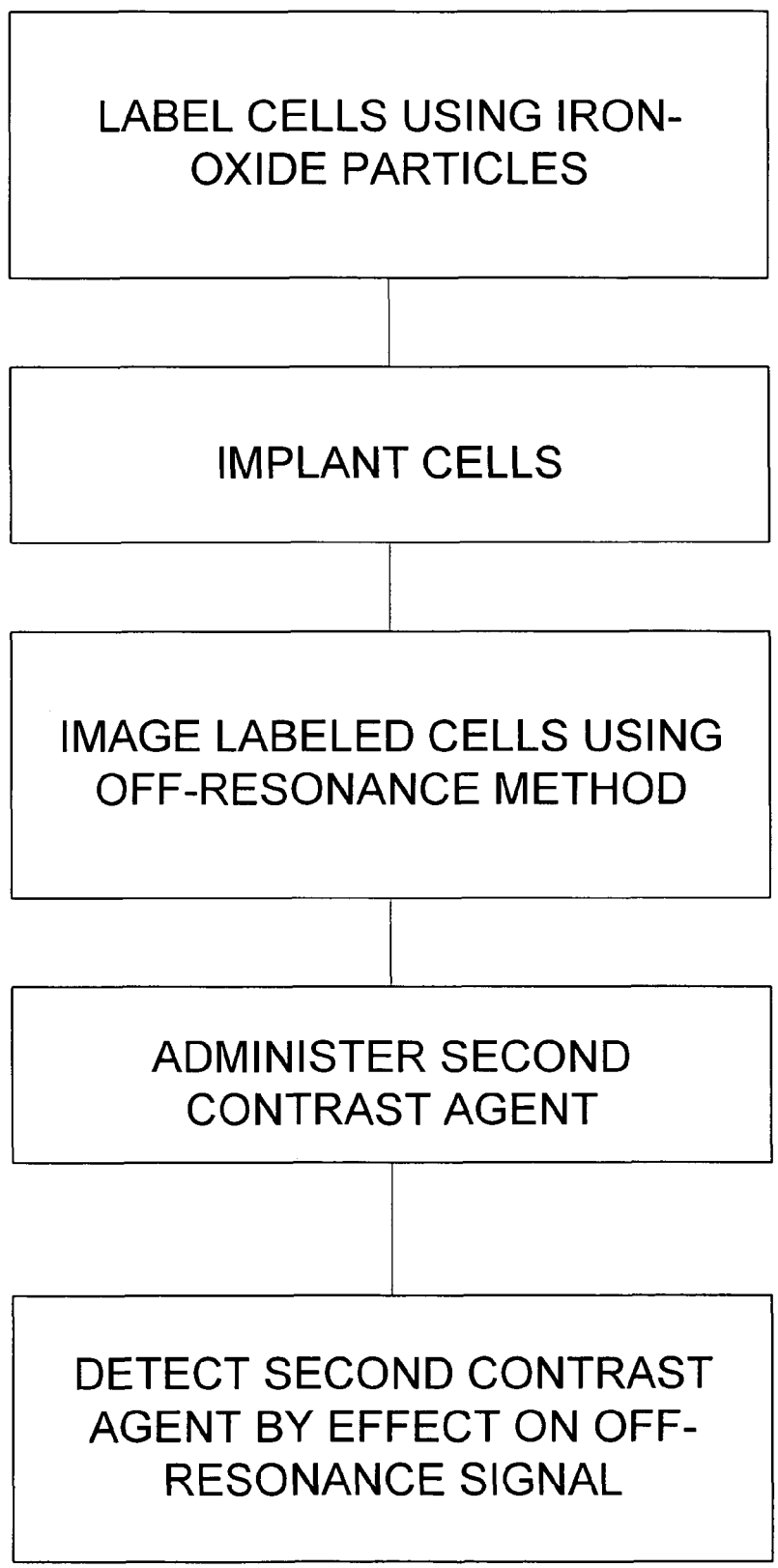
FIG. 3 is a flow diagram illustrating an embodiment of the present invention.

An embodiment of the invention is illustrated in the flow diagram of FIG. 3. As shown at 10, cells are labeled using iron oxide particles such as Feridix or micro-particles or Bang's particles. The labeled cells are them implanted in vivo as shown at 12.

Optionally, a sufficient time delay can be allowed for cell engraftment and differentiation.

The labeled cells are then imaged at 14 using the off-resonance method of application Ser. No. 10/849,068. A second contrast agent is then administrated at 16. This agent can be gadolinium-DTPA attached to an antibody, or the agent can be metabolically active, such as a compound containing hyperpolarized carbon-13 or other T1 shortening agent such as Combidex.

The second agent is then detected at 18 by observation of the effect on the off resonance signal, such as shortening T1 of the imaged cells.

One application of the invention is molecular imaging to detect the presence of specific molecules such as binding receptors on cell surfaces in vivo. One application of such detection is to test whether stem cells have differentiated into the desired tissue at the site of the therapy, by looking for receptors that are present only after differentiation (reporter ligands). While some success has been achieved using gadolinium-based agents attached to the biding molecules, the resulting signal changes are small and very difficult to detect in vivo.

As described earlier, the spectrally selective RF pulses employed in the off-resonance method enable suppression of signal outside the passband by a factor of $10^6$ or greater. This level of background suppression enables the detection of changes in the off-resonance signal that would otherwise be obscured by the background signal.

The high degree of background suppression enables the use of the invention in a non-imaging mode, whereby the spatial localization of the signal is achieved solely by the spectral selectivity of the method. In this mode, the received signal is attributed solely to the spatial region surrounding the labeled cells or materials. The advantage of this is that measurements can be made in rapid temporal succession, giving temporal information that would be impossible to achieve with an imaging method.

With the high temporal rate of measurements possible with the invention, the effects of other contrast agents on the off-resonance signal can be temporally resolved to measure the kinetics of these other agents as they interact with the tissue or structures surrounding the labeled cells or materials. For example, the invention could be used in non-imaging mode to measure the kinetics of the T1-shortening agent Gd-DTPA as it passes through the microvasculature surrounding a transplant of stem cells, which would give information about the structure and extent of these vessels.

While the invention has been described with reference to specific embodiments, the description is illustrative of the invention and is not to be construed as limiting the invention. For Example, other tissue parameters other than thin relaxation time can be measured in the off-resonance signal, such as diffusion coefficient (D), perfusion or rate that blood flows through a given volume (in L/min.), and oxygenation which is the percentage of maximum (saturated) oxygen load that the blood is carrying (i.e., venous blood has low oxygenation and arterial blood has high oxygenation).

Further, a dual or multiple action contrast agent can be attached on the same moiety where the second contrast agent, to be detected in the off-resonance signal, need not necessarily be a separate agent. For example, a T1 shortening molecule such as Gadolinium—DTPA could be attached to an iron-oxide agent so that the T1 of the off-resonance signal is shortened by the action of the Gadolinium atoms. A preferred embodiment of such a dual-action agent could be switched on and off by a third agent, with the changing signal measured at a high tempered rate using the off-resonance signal in "non-imaging" mode.

Thus, various modifications and applications may occur to those skilled in the art without departing from the spirit and scope of the invention as defined by the appended claims.

What is claimed is:

1. A method of imaging contrast agents in a body using magnetic resonance imaging (MR) comprising the steps of:
   a) labeling cells with a first contrast agent with magnetic susceptibility sufficient to induce magnetic field inhomogeneity in water molecules near the first contrast agent,
   b) implanting the cells in the body,
   c) obtaining first MR signals from the water molecules using off-resonance MR,
   d) administering a second contrast agent to the body,
   e) obtaining second MR signals from the water molecules using off-resonance MR, and
   f) detecting the presence of the second contrast agent by comparing the first MR signals and the second MR signals.

2. The method of claim 1 wherein in step f) changes in a magnetic resonance parameter are identified.

3. The method of claim 2 wherein the magnetic resonance parameter is selected from the group consisting of relaxation time T1, diffusion coefficient D, magnetization transfer perfusion, and oxygenation.

4. The method of claim 2 wherein the first contrast agent comprises iron-oxide.

5. The method of claim 4 wherein the iron-oxide comprises iron-oxide nanoparticles.

6. The method of claim 4 wherein the iron-oxide comprises iron-oxide microparticles.

7. The method of claim 4 wherein the second contrast agent comprises gadolinium.

8. The method of claim 4 wherein the second contrast agent comprises a T1 shortening agent.

9. The method of claim 8 wherein the second contrast agent comprises hyperpolarized carbon-13.

10. The method of claim 8 wherein steps c) and e) employ a RF excitation pulse sequence that is spectrally and spatially selective.

11. The method of claim 10 wherein bandwidth of the RF excitation pulse sequence is selected to limit the magnetically field shifted water molecules.

12. The method of claim 11 wherein the RF excitation pulse creates a spin echo signal from the excited water molecules.

13. The method of claim 12 wherein the spin echo time is selected to limit effects of water molecule diffusion.

14. The method of claim 13 wherein spin echo time is balanced with excitation close to a center frequency of the RF signal.

15. The method of claim 1 wherein the second contrast agent is bound to cells labeled with the first contrast agent.

16. The method of claim 1 wherein temporal dynamics of the second contrast agent attachment or detachment are resolved.

17. The method of claim 1 wherein the spectrum of the off-resonance signal is resolved by spectroscopic imaging methods.

18. The method of claim 1 wherein step a) includes use of multiple action contrast agents attached on a same moiety.

\* \* \* \* \*